United States Patent
Fushimi et al.

(10) Patent No.: US 10,180,480 B2
(45) Date of Patent: Jan. 15, 2019

(54) MAGNETIC RESONANCE IMAGING APPARATUS AND IMAGE PROCESSING APPARATUS

(71) Applicants: KYOTO UNIVERSITY, Kyoto-shi, Kyoto (JP); TOSHIBA MEDICAL SYSTEMS CORPORATION, Otawara-shi, Tochigi (JP)

(72) Inventors: Yasutaka Fushimi, Kyoto (JP); Naotaka Sakashita, Tochigi (JP)

(73) Assignee: TOSHIBA MEDICAL SYSTEMS CORPORATION, Otawara-Shi, Tochigi (JP)

(*) Notice: Subject to any disclaimer, the term of this patent is extended or adjusted under 35 U.S.C. 154(b) by 480 days.

(21) Appl. No.: 14/463,023

(22) Filed: Aug. 19, 2014

(65) Prior Publication Data

US 2015/0054508 A1 Feb. 26, 2015

(30) Foreign Application Priority Data

Aug. 20, 2013 (JP) ................................. 2013-170529

(51) Int. Cl.
*G01R 33/56* (2006.01)
*A61B 5/055* (2006.01)
(Continued)

(52) U.S. Cl.
CPC .......... *G01R 33/5608* (2013.01); *A61B 5/055* (2013.01); *A61B 5/4566* (2013.01);
(Continued)

(58) Field of Classification Search
CPC ............ G01R 33/5608; G01R 33/5602; G01R 33/5617; G01R 33/5673; A61B 5/055;
(Continued)

(56) References Cited

U.S. PATENT DOCUMENTS 6,073,041 A * 6/2000 Hu .................. A61B 5/055
324/309
7,577,472 B2 * 8/2009 Li .................... A61B 5/055
128/922
(Continued)

FOREIGN PATENT DOCUMENTS

| JP | H04-067849 A | 3/1992 |
| JP | 2011-092670 | 5/2011 |
| JP | 2012-040310 A | 3/2012 |

OTHER PUBLICATIONS

F. Braga et al., "Relationship Between the Concentration of Supplemental Oxygen and Signal Intensity of CSF Depicted by Fluid-Attenuated Inversion Recovery Imaging", American Society of Neuroradiology, AJNR Am J Neuroradiol 24: Oct. 2003, pp. 1863-1868.

(Continued)

*Primary Examiner* — Ruifeng Pu

(74) *Attorney, Agent, or Firm* — Nixon & Vanderhye P.C.

(57) ABSTRACT

A magnetic resonance imaging apparatus according to an embodiment includes a sequence controller and a storage unit. The sequence controller acquires magnetic resonance signals of a target imaging part including cerebrospinal fluid flowing therein of a subject in a condition where a supply of oxygen is receivable, at a plurality of time phases in an oxygen inhalation process of the subject. The storage unit stores therein the magnetic resonance signals acquired at the time phases.

13 Claims, 14 Drawing Sheets

(51) Int. Cl.
*A61B 5/00* (2006.01)
*G01R 33/567* (2006.01)
*G01R 33/561* (2006.01)
*A61B 5/145* (2006.01)

(52) U.S. Cl.
CPC ........ *A61B 5/7289* (2013.01); *A61B 5/14507* (2013.01); *A61B 5/14542* (2013.01); *G01R 33/5602* (2013.01); *G01R 33/5617* (2013.01); *G01R 33/5673* (2013.01)

(58) Field of Classification Search
CPC . A61B 5/4566; A61B 5/7289; A61B 5/14542; A61B 5/14507; A61B 5/5602
See application file for complete search history.

(56) References Cited

U.S. PATENT DOCUMENTS

| | | | | |
|---|---|---|---|---|
| 2002/0188190 | A1* | 12/2002 | Kassai | G01R 33/5673 600/410 |
| 2009/0221901 | A1* | 9/2009 | Yamamoto | A61B 5/055 600/410 |
| 2010/0259263 | A1* | 10/2010 | Holland | A61B 5/055 324/310 |
| 2014/0121495 | A1* | 5/2014 | Dempsey | A61N 5/1064 600/411 |
| 2014/0270451 | A1* | 9/2014 | Zach | A61B 5/055 382/131 |
| 2015/0204956 | A1* | 7/2015 | Remmele | G01R 33/50 382/131 |
| 2015/0309134 | A1* | 10/2015 | Meakin | A61B 5/0263 324/309 |
| 2016/0109539 | A1* | 4/2016 | Mardor | G01R 33/5608 600/420 |
| 2016/0157746 | A1* | 6/2016 | Ellingson | A61B 5/055 600/420 |

OTHER PUBLICATIONS

Japanese office action dated Jul. 11, 2017, in Patent Application No. JP 2013-170529.
Yoshimi Anzai et al. "Paramagnetic Effect of Supplemental Oxygen on CSF Hyperintensity on Fluid-Attenuated Inversion Recovery MR Images," AJNR Am J Neuroradiol, 25:274-279, Feb. 2004.
Japanese office action dated Feb. 27, 2018, in Patent Application No. JP 2013-170529.

* cited by examiner

Pre-O2 minus O2

Post-O2 minus O2

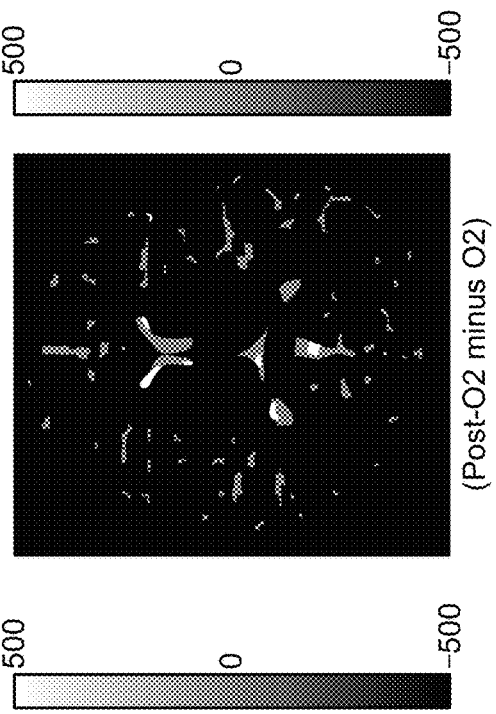
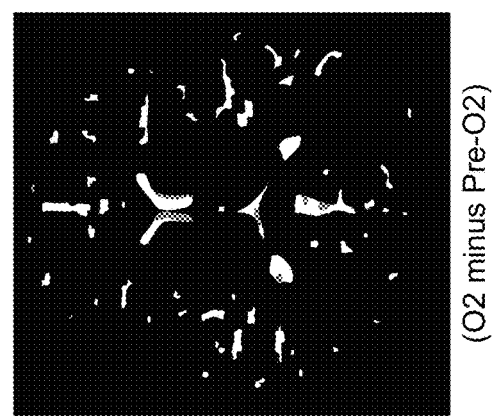
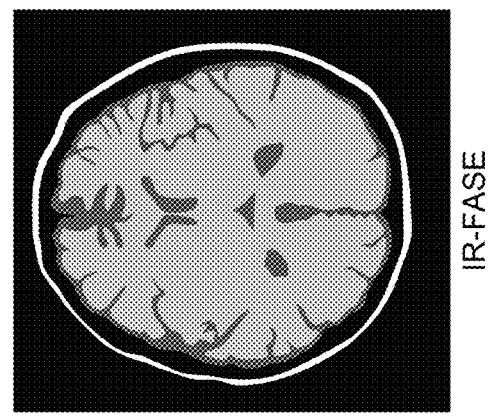
FIG.10A  IR-FASE
FIG.10B  (O2 minus Pre-O2)
FIG.10C  (Post-O2 minus O2)

MAGNETIC RESONANCE IMAGING APPARATUS AND IMAGE PROCESSING APPARATUS

CROSS-REFERENCE TO RELATED APPLICATIONS

This application is based upon and claims the benefit of priority from Japanese Patent Application No. 2013-170529, filed on Aug. 20, 2013; the entire contents of which are incorporated herein by reference.

FIELD

Embodiments described herein relate generally to a magnetic resonance imaging apparatus and an image processing apparatus.

BACKGROUND

Magnetic resonance imaging (MRI) is an imaging method by which a nuclear spin in a subject placed in a magnetostatic field is magnetically excited with a radio frequency (RF) pulse at a Larmor frequency so that an image is generated from magnetic resonance signals generated due to the excitation.

In the field of magnetic resonance imaging, contrast enhancement by oxygen has been known. For example, an imaging method called the fluid attenuated inversion recovery (FLAIR) method has been known in which the time period between when an inversion pulse is applied and when the longitudinal magnetic component of cerebrospinal fluid (CSF) becomes zero is set as an inversion time (TI). It has been reported that the contrast of CSF changes when imaging is performed by the FLAIR method while oxygen is supplied.

BRIEF DESCRIPTION OF THE DRAWINGS

FIGS. 10A, 10B, and 10C are diagrams for explaining subtracted images in the first embodiment;

DETAILED DESCRIPTION

A magnetic resonance imaging apparatus according to one embodiment includes a sequence controller and a storage unit. The sequence controller acquires magnetic resonance signals of a target imaging part including cerebrospinal fluid flowing therein of a subject in a condition where a supply of oxygen is receivable, at a plurality of time phases in an oxygen inhalation process of the subject. The storage unit stores therein the magnetic resonance signals acquired at the time phases.

Embodiments of a magnetic resonance imaging (MRI) apparatus and an image processing apparatus will be explained with reference to the accompanying drawings. The embodiments, however, are not limited to those described in the following. Description of each embodiment is similarly applicable to the other embodiments in principle.

First Embodiment

Figure 1:
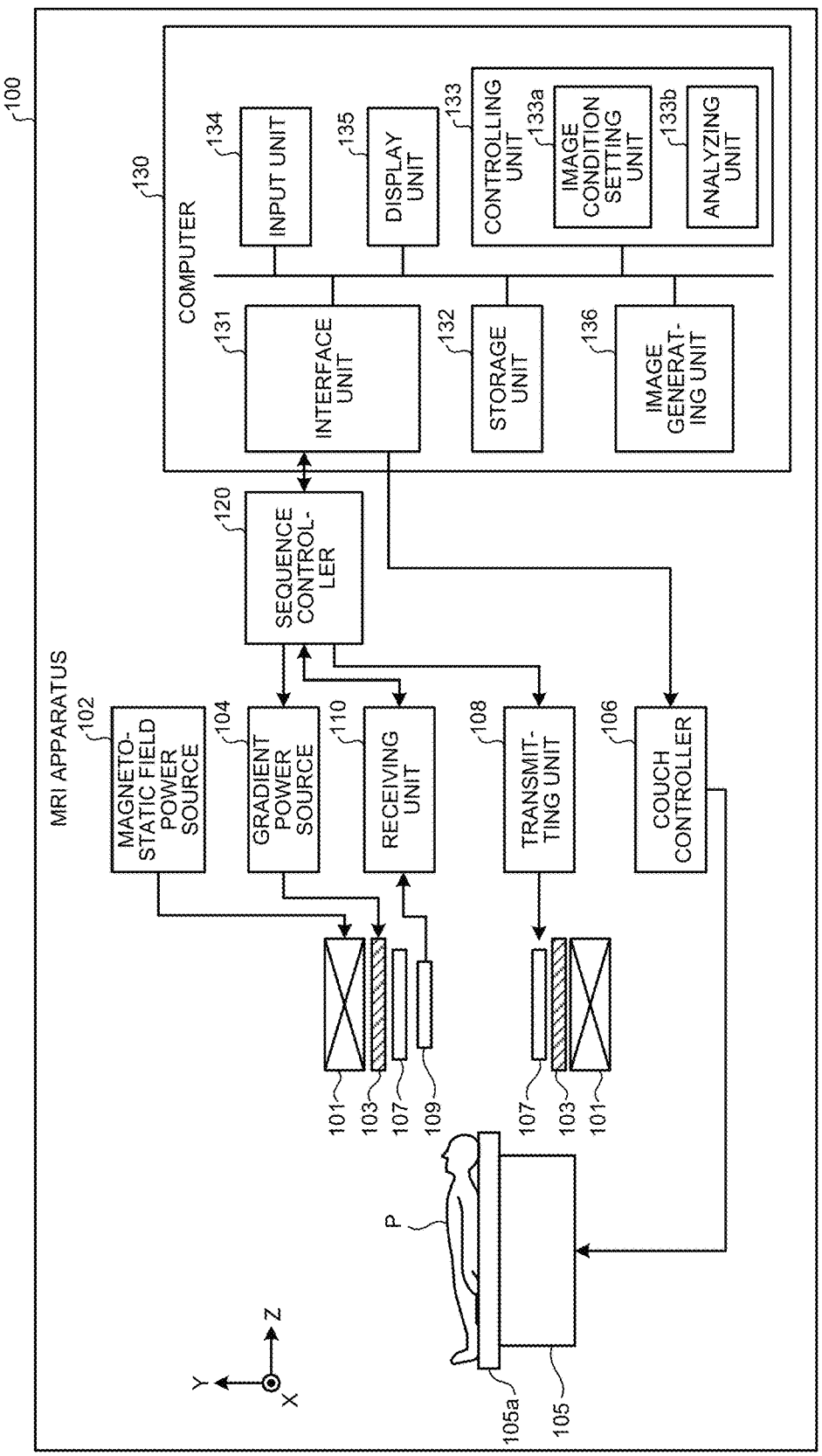
FIG. 1 is a functional block diagram of an MRI apparatus according to a first embodiment.

FIG. 1 is a functional block diagram of an MRI apparatus 100 according to a first embodiment. As illustrated in FIG. 1, the MRI apparatus 100 includes a magnetostatic field magnet 101, a magnetostatic field power source 102, a gradient coil 103, a gradient power source 104, a couch 105, a couch controller 106, a transmission coil 107, a transmitting unit 108, a reception coil 109, a receiving unit 110, a sequence controller 120, and a computer 130. The MRI apparatus 100 does not include a subject P (e.g., a human body). In addition, FIG. 1 illustrates merely an example configuration. For example, units in the sequence controller 120 and the computer 130 may be integrated or distributed as appropriate.

The magnetostatic field magnet 101 is a magnet formed in the shape of a hollow circular cylinder and generates a magnetostatic field in the space inside thereof. The magnetostatic field magnet 101 is, for example, a superconductive magnet and is excited with an electric current supplied from the magnetostatic field power source 102. The magnetostatic field power source 102 supplies an electric current to the magnetostatic field magnet 101. The magnetostatic field magnet 101 may be a permanent magnet. In this case, the MRI apparatus 100 does not have to include the magnetostatic field power source 102. The magnetostatic field power source 102 may be provided separately from the MRI apparatus 100.

The gradient coil 103 is a coil formed in the shape of a hollow circular cylinder and is disposed inside the magnetostatic field magnet 101. The gradient coil 103 is formed by combining three coils corresponding to X-, Y-, and Z-axes that are orthogonal to one another. These three coils individually receive an electric current from the gradient power source 104 and generate gradient magnetic fields of which the magnetic field intensities change along the X-, Y-, and Z-axes. The gradient power source 104 supplies an electric current to the gradient coil 103.

The couch 105 includes a couchtop 105a on which the subject P is placed. Under the control of the couch controller 106, the couchtop 105a is inserted into the hollow (an imaging opening) of the gradient coil 103 while the subject P is placed thereon. Normally, the couch 105 is provided such that the longitudinal direction thereof extends parallel to the central axis of the magnetostatic field magnet 101.

Under the control of the computer 130, the couch controller 106 drives the couch 105 so that the couchtop 105a moves in the longitudinal direction and in an up-and-down direction.

The transmission coil 107 is disposed inside the gradient coil 103 and generates a radio-frequency magnetic field by receiving a supply of an RF pulse from the transmitting unit 108. The transmitting unit 108 supplies the RF pulse corresponding to a Larmor frequency, which is determined by the type of a target atom and the intensity of the magnetic field, to the transmission coil 107.

The reception coil 109 is disposed inside the gradient coil 103 and receives magnetic resonance (MR) signals emitted from the subject P due to an influence of the radio-frequency magnetic field. When having received the MR signals, the reception coil 109 outputs the received MR signals to the receiving unit 110.

The transmission coil 107 and the reception coil 109 described above are merely examples. The embodiment may be configured with one coil or a combination of two or more coils among coils having only transmission function, only reception function, and transmission and reception functions.

The receiving unit 110 detects the MR signals output from the reception coil 109 and generates MR data based on the detected MR signals. Specifically, the receiving unit 110 generates the MR data by applying a digital conversion to the MR signals output from the reception coil 109. Furthermore, the receiving unit 110 transmits the generated MR data to the sequence controller 120. The receiving unit 110 may be provided on a gantry device side where the magnetostatic field magnet 101, the gradient coil 103, and the like are provided.

The sequence controller 120 executes a pulse sequence by driving the gradient power source 104, the transmitting unit 108, and the receiving unit 110 based on sequence information transmitted from the computer 130 to take an image of the subject P. In this situation, the sequence information is information that defines a procedure for performing the imaging process. The sequence information defines, for example, the intensity of the electric current supplied by the gradient power source 104 to the gradient coil 103 and the timing with which the electric current is supplied, the strength of the RF pulse supplied by the transmitting unit 108 to the transmission coil 107 and the timing with which the RF pulse is applied, and the timing with which the MR signals are detected by the receiving unit 110. For example, the sequence controller 120 may be a processor such as a central processing unit (CPU) or a micro processing unit (MPU).

When having received the MR data from the receiving unit 110 as a result of driving the gradient power source 104, the transmitting unit 108, and the receiving unit 110 and taking an image of the subject P, the sequence controller 120 transfers the received MR data to the computer 130.

The computer 130 performs overall control of the MRI apparatus 100 and generates MR images, for example. The computer 130 includes an interface unit 131, a storage unit 132, a controlling unit 133, an input unit 134, a display unit 135, and an image generating unit 136.

The interface unit 131 transmits the sequence information to the sequence controller 120 and receives the MR data from the sequence controller 120. When having received the MR data, the interface unit 131 stores the received MR data into the storage unit 132. The MR data stored in the storage unit 132 is arranged into a k-space by the controlling unit 133. As a result, the storage unit 132 stores therein k-space data.

The storage unit 132 stores therein, for example, MR data received by the interface unit 131, k-space data of the k-space arranged by the controlling unit 133, and image data generated by the image generating unit 136. For example, the storage unit 132 may be a semiconductor memory element such as a random access memory (RAM) or a flash memory, a hard disk, an optical disc, or the like.

The input unit 134 receives various types of instructions and inputs of information from an operator. The input unit 134 may be a pointing device such as a mouse or a trackball, or an input device such as a keyboard. Under the control of the controlling unit 133, the display unit 135 displays a graphical user interface (GUI) for receiving an input of an imaging condition, an MR image generated by the image generating unit 136, and the like. The display unit 135 may be, for example, a display device such as a liquid crystal monitor.

The controlling unit 133 performs overall control of the MRI apparatus 100 and controls an imaging process, generation of an MR image, and display of the MR image, for example. For example, the controlling unit 133 may be a processor such as a CPU or an MPU. As illustrated in FIG. 1, the controlling unit 133 includes an imaging condition setting unit 133a and an analyzing unit 133b. The imaging condition setting unit 133a receives an input of an imaging condition via the GUI and generates sequence information based on the received imaging condition. The imaging condition setting unit 133a also transmits the generated sequence information to the sequence controller 120.

The analyzing unit 133b extracts, from an MR image corresponding to each of the time phases, individual regions (e.g., the region of a cerebral sulcus portion and the region of a cerebral ventricle portion) obtained by further segmenting a CSF region where CSF is present, and analyzes each of the extracted regions. The analyzing unit 133b also calculates a statistical value (e.g., an average value) of signal values of the CSF in each of the individual regions, generates a graph with the calculated statistical values plotted in time series, and displays the generated graph on the display unit 135. Furthermore, the analyzing unit 133b calculates a subtracted image of MR images corresponding to at least two respective time phases, and displays the calculated subtracted image on the display unit 135. Details of the process performed by the analyzing unit 133b will be explained later.

The image generating unit 136 generates an MR image by reading k-space data from the storage unit 132 and applying a reconstructing process such as a Fourier transform process to the read k-space data.

The first embodiment exemplifies imaging of dynamics of CSF by taking a "brain" as a target imaging part. Specifically, the sequence controller 120 according to the first embodiment acquires slice images (two-dimensional cross-sectional images) of the brain of a subject in a condition where a supply of oxygen is receivable, at a plurality of time phases in an oxygen inhalation process, in order to understand the dynamics of CSF in the oxygen inhalation process. Here, the oxygen inhalation process means a period that includes at least one period of periods before, during, and after oxygen inhalation. For example, the oxygen inhalation process is defined as a series of periods before, during, and after oxygen inhalation.

Figure 2:
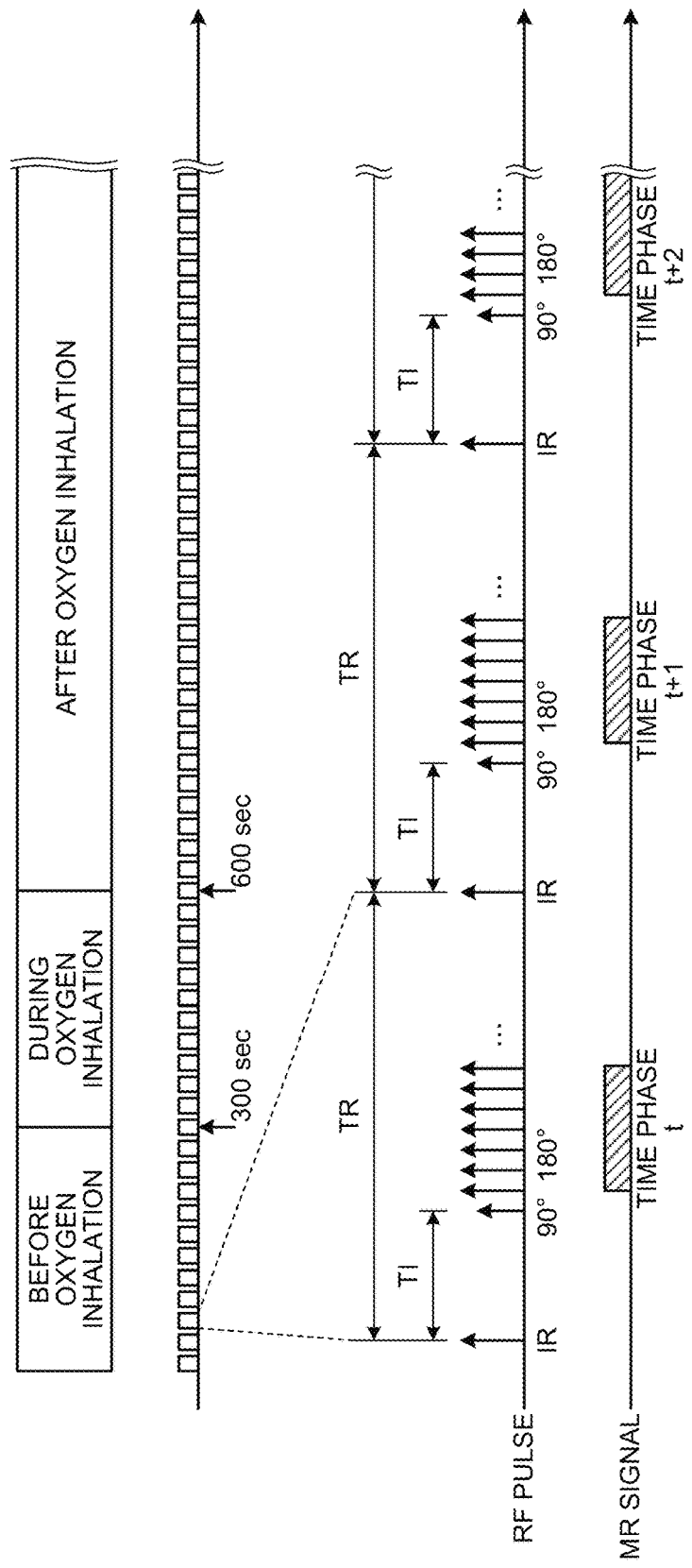
FIG. 2 is a diagram for explaining a pulse sequence in the first embodiment.

FIG. 2 is a diagram for explaining a pulse sequence in the first embodiment. FIG. 2 indicates timings with which RF pulses are applied, omitting the slice selection gradient, the readout gradient, and the phase encoding gradient. As illustrated in FIG. 2, in the first embodiment, the sequence controller 120 repeatedly acquires slice images of the brain at a time resolution of about several seconds to several tens of seconds for the entire oxygen inhalation process including before and after oxygen inhalation. FIG. 2 illustrates a configuration in which the elapsed time at the start of oxygen inhalation is "300 sec" and the elapsed time at the stop of oxygen inhalation is "600 sec". However, the configuration is merely an example.

The first embodiment exemplifies a pulse sequence based on the fast asymmetric spin echo (FASE) method with an inversion recovery (IR) pulse to invert the longitudinal magnetization. As illustrated in FIG. 2, during each repetition time (TR), the sequence controller 120 applies an IR pulse (non-region-selecting and non-frequency-selecting IR pulse) after a certain delay time has elapsed from an occurrence of a trigger signal (not illustrated) (e.g., a biological signal such as an electrocardiogram signal, a pulse-wave signal, and a respiratory signal, or a clock of the MRI apparatus 100). This reverses the longitudinal magnetization of tissues in an imaging region, and thus also reverses the longitudinal magnetization of CSF in the imaging region.

After applying the IR pulse, the sequence controller 120 applies, to the imaging region, an excitation pulse (e.g., 90°) after a certain TI has elapsed and then refocus pulses (e.g., 180°) repeatedly. The application of the refocus pulses generates a plurality of MR signals successively. For a single shot by the FASE method, different phase encodes are given to the respective MR signals acquired during one TR, and one slice image is reconstructed from the MR signals acquired during the one TR. In the first embodiment, the TI is set to an appropriate value by referencing the T1 value of the CSF as described later. In the first embodiment, the TR is specified as several seconds to several tens of seconds. This is a time resolution at which a temporal change in the signal values of the CSF during oxygen inhalation can be analyzed. However, possible TRs are not limited to that described in the embodiment. The TR may be set to an appropriate value for a time resolution required for observing the dynamics of CSF, in view of the recovery of the longitudinal magnetization of CSF and a fast imaging method, for example.

As illustrated in FIG. 2, the sequence controller 120 repeats the above-described imaging to repeatedly acquire the slice images of the brain corresponding to a time phase t, a time phase t+1, a time phase t+2, and so on, for the entire oxygen inhalation process including before and after oxygen inhalation. When performing imaging in response to a trigger signal, the sequence controller 120 repeats the above-described imaging of the same slice after a certain delay time (a common delay time) has elapsed from the occurrence of the trigger signal. This can provide a plurality of tomographic images of the same slice position and the same imaging timing at different time phases by using a trigger signal. In other words, the slice images of the brain are repeatedly acquired for predetermined periods, such as the time phase t, the time phase t+1, the time phase t+2, and so on, for the entire oxygen inhalation process including before and after oxygen inhalation.

Figure 3:
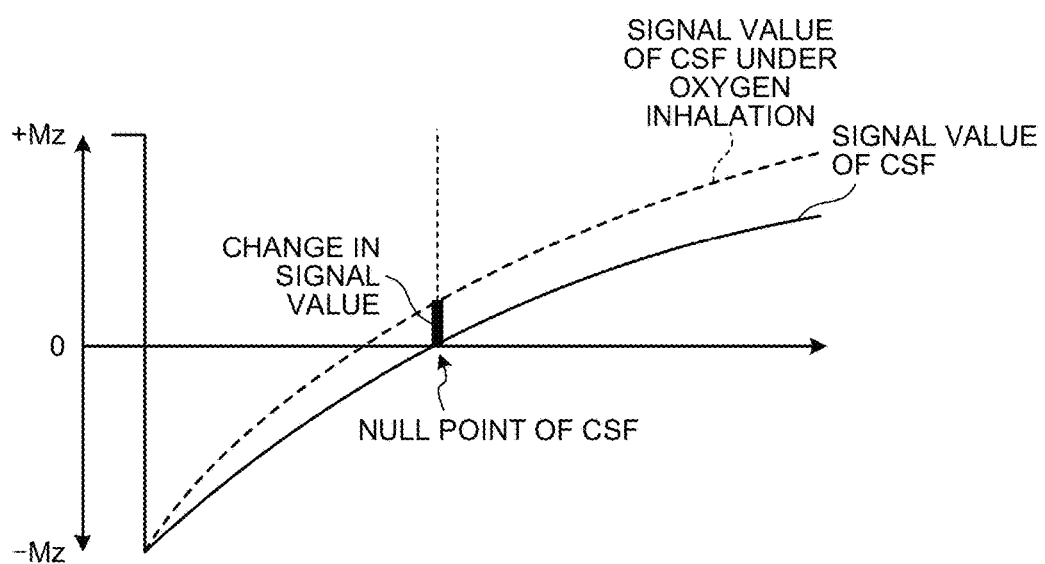
FIG. 3 is a diagram for explaining signal values of CSF in the first embodiment.

FIG. 3 is a diagram for explaining signal values of CSF according to the first embodiment. As described above, in the first embodiment, the TI is set to an appropriate value by referencing the T1 value of the CSF. Specifically, applying an IR pulse without selecting a region reverses the longitudinal magnetization of CSF in an imaging region from "+Mz" to "−Mz" as illustrated in FIG. 3. Thereafter, the longitudinal magnetization of the CSF gradually recovers and eventually reaches a null point where the longitudinal magnetization becomes zero. The time from the reverse of the longitudinal magnetization to the null point corresponds to "the T1 value of the CSF", which is calculated from the T1 value of the CSF or set to an appropriate value by a preparation scan described later.

The contrast enhancement by oxygen is considered to be an effect of oxygen that reduces the T1 value. That is, in the CSF during oxygen inhalation, the longitudinal magnetization recovers faster and a timing of the null point is earlier as indicated by the dotted line in FIG. 3. If imaging is performed with the TI set by referencing the T1 value of the CSF not under oxygen inhalation, the CSF during oxygen inhalation has a signal value at the null point of the CSF not under oxygen inhalation. This results in a change (difference) between the signal values under oxygen inhalation and those not under oxygen inhalation as illustrated in FIG. 3. The first embodiment focuses on the change of the signal values of CSF under oxygen inhalation. To actively visualize the region in which CSF is present, imaging is performed with the TI set by referencing the T1 value of the CSF not under the oxygen inhalation. This may be considered as setting the TR based on the T1 value of the CSF. The T1 value of the CSF is 1,000 milliseconds or longer, and the TR is preferably set to a value larger than the T1 value. An effective echo time (TE) may be any value, and may be set to a time point near the null point of the CSF, for example. When an IR pulse is not applied, the TR does not have to be set larger than the T1 value. However, it is preferably set to an optimal value corresponding to the T1 value.

Figure 4:
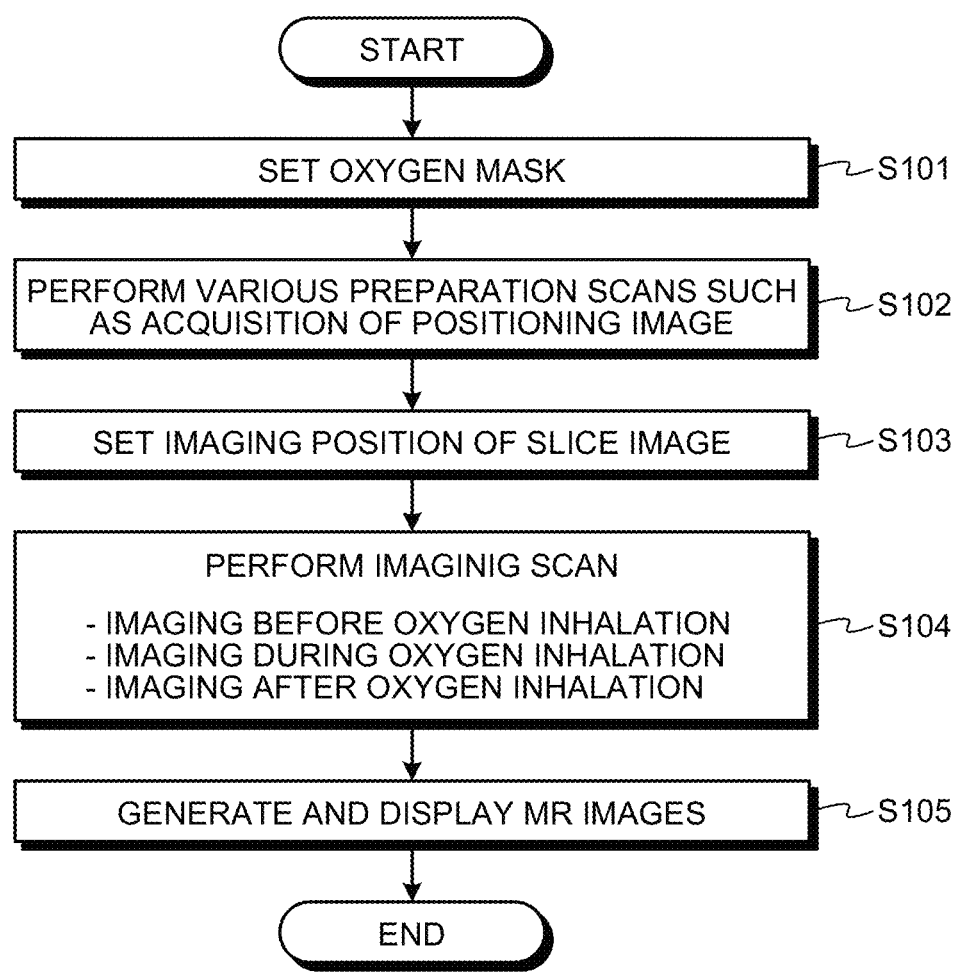
FIG. 4 is a flow chart illustrating a processing procedure of imaging in the first embodiment.

FIG. 4 is a flow chart illustrating a processing procedure of imaging in the first embodiment. Typically, before the processing illustrated in FIG. 4, an operator has selected a series of protocols (e.g., a protocol for acquiring a positioning image, a protocol for imaging a sensitivity map, a protocol for shimming imaging, and a protocol for an imaging scan) for acquiring MR images of a brain through a GUI for inputting an imaging condition. The sequence controller 120 performs various processing illustrated in FIG. 4 according to the selected protocols.

As described above, in the first embodiment, it is assumed that imaging is performed while a subject P is made inhale oxygen. As illustrated in FIG. 4, the subject P puts on an oxygen mask and prepared to be supplied with oxygen through a tube from, for example, an oxygen tank provided outside a shielded room (Step S101). The oxygen mask is set in a fully sealed manner so that air is not mixed in from the outside. In addition, the supply of oxygen should be adjustable from the outside.

The method of supplying the subject P with oxygen is not limited to that with an oxygen mask, and various other methods can be used.

The sequence controller 120 subsequently acquires positioning images and performs various preparation scans such as sensitive map imaging and shimming imaging (Step S102). For example, the sequence controller 120 images a coronal image and a sagittal image of the brain of the subject P as positioning images for setting an imaging position of a slice image of the brain, and displays the positioning images on the display unit 135. On the positioning images displayed on the display unit 135, for example, an operator specifies an imaging position of a slice image, and the imaging condition setting unit 133a sets the specified imaging position as the imaging position of the slice image (Step S103).

In the first embodiment, the imaging position of the slice image is set to a position, for example, where a typical axial image of the brain can be acquired. For example, the imaging position is set to a position on an anterior commissure (AC)-posterior commissure (PC) line that connects the upper end of the AC and the lower end of the PC, a position on a line obtained by slightly tilting the Sylvian fissure on the sagittal image, or a position where main structures of the brain, such as the thalamus and the basal ganglia, and the corpus callosum, are acquired in an image.

Subsequently, the sequence controller 120 performs an imaging scan (Step S104). For example, in the first embodiment, the sequence controller 120 executes a pulse sequence based on the FASE method with an IR pulse, for the imaging position set at Step S103 as an imaging region. In the first embodiment, the sequence controller 120 repeatedly acquires slice images of the brain for the entire oxygen inhalation process including before and after oxygen inhalation. The sequence controller 120, as illustrated in FIG. 2, therefore allows sufficient time required to observe the dynamics of the CSF for each of the "before oxygen inhalation" period before oxygen inhalation starts, the "during oxygen inhalation" period during oxygen inhalation, and the "after oxygen inhalation" period after oxygen inhalation stops.

For example, during imaging for 1,200 seconds, oxygen supply to the subject P starts when 300 seconds has elapsed, and the oxygen supply to the subject P stops when 600 seconds has elapsed. The timings of a start and a stop of the oxygen supply may be controlled manually by an operator, or preliminary set as an imaging condition and controlled automatically together with an oxygen supply device.

MR data thus acquired under the control by the sequence controller 120 is transmitted to the computer 130, and then the image generating unit 136 of the computer 130 generates an MR image and displays the MR image on the display unit 135 (Step S105).

The processing procedure of imaging in the first embodiment has been described above; however, it is not limited to that described in the embodiment. The processing procedure of imaging may be modified as appropriate depending on the form of operation or other conditions. For example, an examination in which the "brain" is a target imaging part typically includes a plurality of imaging scans. In other words, in the one examination, various imaging scans are continually performed with an operation by an operator interposed as appropriate. The various imaging scans may include not only the imaging scan illustrated in FIG. 2 that is performed during oxygen inhalation, but also an imaging scan that acquires a three-dimensional T1 weighted image of the entire brain without oxygen inhalation, and an imaging scan that similarly acquires a three-dimensional T2 weighted image of the entire brain without oxygen inhalation.

In these cases, for example, the setting of an imaging position at Step S103 in FIG. 4 does not have to be performed on the positioning images acquired at Step S102. The setting of an imaging position may be performed on an MR image acquired and generated by an imaging scan at the previous stage among the imaging scans performed continually. In addition, the generation and display of an MR image at Step S105 does not have to be performed in the processing procedure of imaging. For example, the generation and display of an MR image may be performed in the processing procedure of analysis described later.

Figure 5:
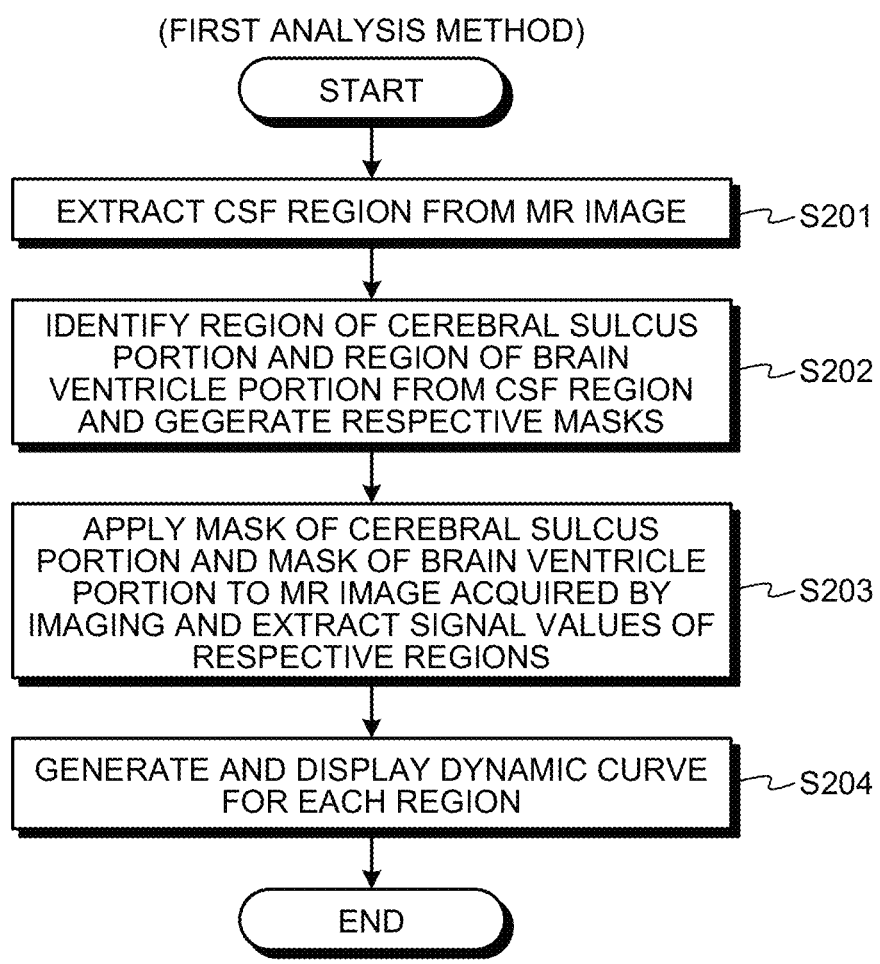
FIG. 5 is a flow chart illustrating a processing procedure of analysis in the first embodiment.

FIG. 5 is a flow chart illustrating a processing procedure of analysis in the first embodiment. Two analysis methods are primarily assumed in the first embodiment, and FIG. 5 illustrates the processing procedure by the first analysis method.

The analyzing unit 133b reads an MR image to be analyzed from the storage unit 132 and performs imaging processing on the read MR image to extract the region (CSF region) where CSF is present from the MR image (Step S201). The MR image used for extracting a CSF region and generating a mask may be one of the MR images corresponding to the respective time phases acquired in the processing procedure of imaging in FIG. 4, an average image of the MR images, or an MR image acquired separately (e.g., a three-dimensional T1 weighted image acquired by a different imaging scan).

For example, the analyzing unit 133b performs an image analysis including four processes, which are realignment, normalization, smoothing, and statistical analysis, with image analysis software called statistical parametric mapping (SPM), and extracts a CSF region from the MR image. Subsequently, the analyzing unit 133b defines the extracted CSF region as a mask f(x,y) of the entire CSF region. For example, with the mask f(x,y), "1" is allocated to pixels in the CSF region, and "0" is allocated to pixels outside the CSF region. The method for extracting a CSF region is not limited to the SPM, and another image analysis method (e.g., threshold operation) may be used.

Subsequently, the analyzing unit 133b identifies the region of a cerebral sulcus portion and the region of a cerebral ventricle portion from the CSF region extracted at Step S201, and generates a mask for the cerebral sulcus portion and a mask for the cerebral ventricle portion separately (Step S202). The region of the cerebral sulcus portion and the region of the cerebral ventricle portion are identified in the CSF region because it is considered that there may be a significant difference between the region where a large amount of oxygen is supplied due to a large number of blood vessels and the region where it is not.

For example, the analyzing unit 133b displays the MR image to be analyzed on the display unit 135 and receives from an operator a specification of a region of interest (ROI) in the form of a circle, for example. A cerebral ventricle portion is relatively easier to visually check, and thus the operator specifies a circle ROI such that it encompasses the cerebral ventricle portion. In response, the analyzing unit 133b multiplies the pixels of the mask f(x,y) of the entire CSF region generated at Step S201 by the respective pixels of a mask g(x,y) of the ROI specified by the operator to generate a mask fv(x,y) of the cerebral ventricle portion. That is, fv(x,y)=f(x,y)×g(x,y), where "×" means multiplication between the respective pixels. With the mask fv(x,y), "1" is allocated to the pixels in the region of the cerebral ventricle portion, and "0" is allocated to the pixels outside the region of the cerebral ventricle portion.

In another example, the analyzing unit 133b subtracts the pixels of the mask fv(x,y) of the cerebral ventricle portion from the mask f(x,y) of the entire CSF region to generate a mask fs(x,y) of the cerebral sulcus portion. That is, fs(x,y)=f(x,y)−fv(x,y), where "−" means subtraction between the respective pixels. With the mask fs(x,y), "1" is allocated to the pixels in the region of the cerebral sulcus portion, and "0" is allocated to the pixels outside the region of the cerebral sulcus portion.

Figure 6:
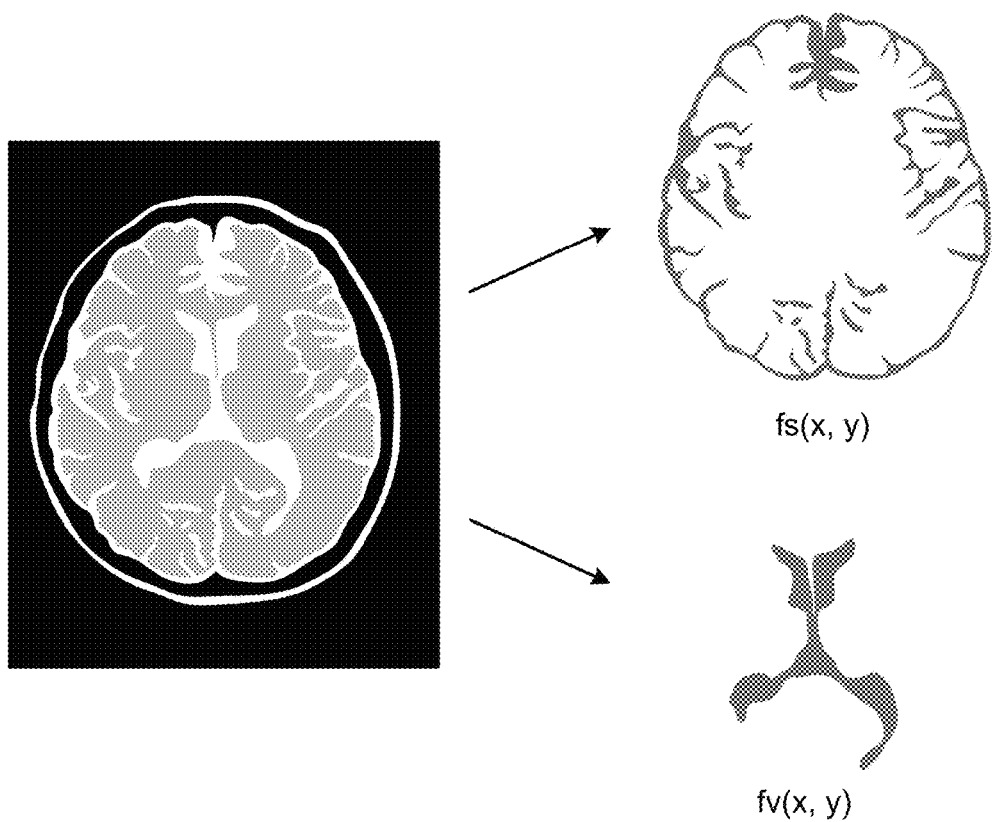
FIG. 6 is a diagram for explaining masks in the first embodiment.

FIG. 6 is a diagram for explaining masks in the first embodiment. For example, as illustrated in FIG. 6, the analyzing unit 133b generates the mask fs(x,y) of the cerebral sulcus portion and the mask fv(x,y) of the cerebral ventricle portion from an MR image.

Subsequently, the analyzing unit 133b applies the mask of the cerebral sulcus portion and the mask of the cerebral ventricle portion generated at Step S202 to each of the MR images corresponding to the respective time phases included in the MR images acquired in the processing procedure of imaging in FIG. 4, and extracts respective signal values of the region of the cerebral sulcus portion and the region of the cerebral ventricle portion from each MR image (Step S203). In other words, the analyzing unit 133b multiplies each of the MR images corresponding to the respective time phases by the mask fs(x,y) of the cerebral sulcus portion and the mask fs(x,y) of the cerebral ventricle portion to extract respective signal values of the region of the cerebral sulcus portion and the region of the cerebral ventricle portion from each MR image.

After that, the analyzing unit 133b generates a graph with the signal values plotted in time series for each region of the cerebral sulcus portion and the cerebral ventricle portion and displays the generated graph on the display unit 135 (Step S204).

Figure 7A:
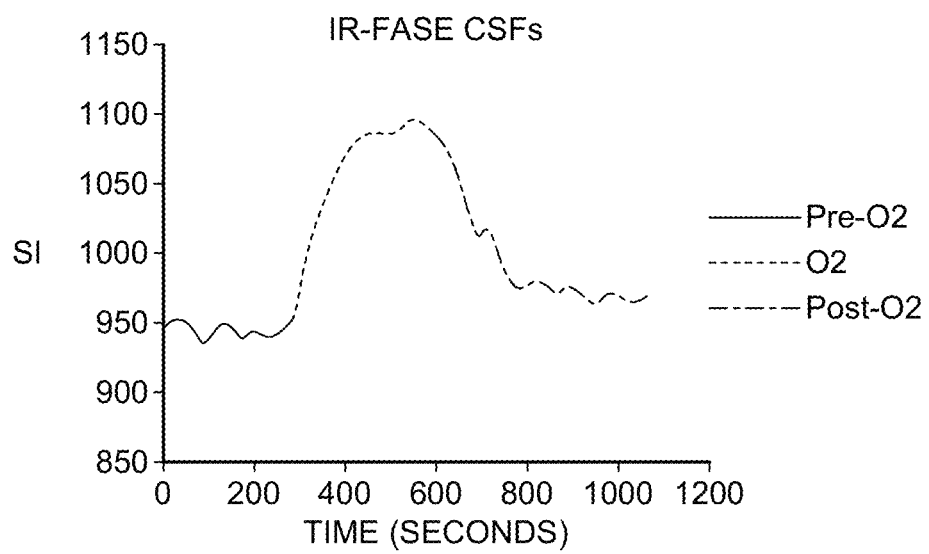
FIGS. 7A and 7B are diagrams for explaining dynamic curves in the first embodiment.
Figure 7B:
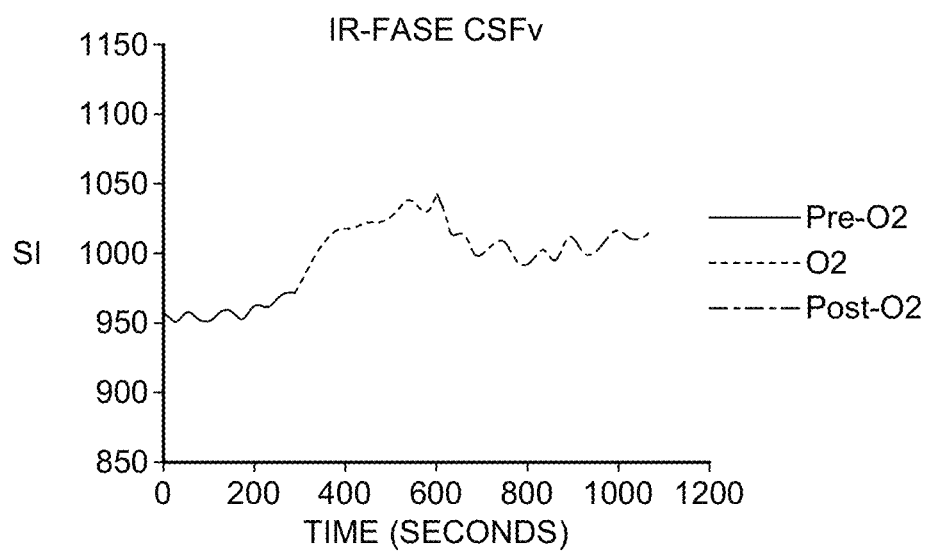

FIGS. 7A and 7B are diagrams for explaining dynamic curves in the first embodiment. For example, the analyzing unit 133b obtains an average value of the signal values (pixel values) in each region of the cerebral sulcus portion and the cerebral ventricle portion, the signals being extracted from each of the MR images. After that, the analyzing unit 133b generates a graph for each region of the cerebral sulcus portion and the cerebral ventricle portion, as illustrated in FIGS. 7A and 7B, taking the signal intensity (SI) as the vertical axis and the elapsed time (second) as the horizontal axis, plots the average value of the pixels corresponding to each of the time phases, and connects the plot points with a line to display a dynamic curve. In the examples illustrated in FIGS. 7A and 7B, the values are normalized with the signal intensity of 1,000. FIG. 7A illustrates a dynamic curve of the region (CSFs) of the cerebral sulcus portion, and FIG. 7B illustrates a dynamic curve of the region (CSFv) of the cerebral ventricle portion.

In FIGS. 7A and 7B, the periods "before oxygen inhalation (Pre-O2)", "during oxygen inhalation (O2)", and "after oxygen inhalation (Post-O2)" are indicated with different types of lines for convenience of explanation; however, the periods may be indicated with lines of different colors. For example, the analyzing unit 133b may use different colors to indicate the dynamic curves, for example, indicating the "before oxygen inhalation (Pre-O2)" dynamic curve with a blue line, the "during oxygen inhalation (O2)" dynamic curve with a red line, and the "after oxygen inhalation (Post-O2)" dynamic curve with a green line.

In another example, the analyzing unit 133b may explicitly indicate the boundary between the "before oxygen inhalation (Pre-O2)" and the "during oxygen inhalation (O2)" and the boundary between the "during oxygen inhalation (O2)" and the "after oxygen inhalation (Post-O2)" with a vertical dotted line.

As illustrated in FIGS. 7A and 7B, it is recognized that a change in the pixel values appears immediately after oxygen inhalation starts. Similarly, it is recognized that a change in the pixel values in the CSF region appears immediately after oxygen inhalation stops. In addition, as illustrated in FIGS. 7A and 7B, the degree of change in the cerebral sulcus portion is larger than that in the cerebral ventricle portion, and it is thus considered that the contrast enhancement by oxygen is larger on the cerebral sulcus portion than on the cerebral ventricle portion. Furthermore, as indicated with the dynamic curve of the cerebral sulcus portion, the pixel values, which increase immediately after oxygen inhalation starts, can be observed as in a saturated state when they reach certain values.

FIGS. 7A and 7B illustrate an example in which a dynamic curve is generated to include all the periods "before oxygen inhalation (Pre-O2)", "during oxygen inhalation (O2)", and "after oxygen inhalation (Post-O2)"; however, possible dynamic curves are not limited to this example. For example, a dynamic curve may be generated that includes any one of or two of the periods. In another example, a dynamic curve may be generated with a reduced number of time phases included in each period. For example, the signal values of the "before oxygen inhalation (Pre-O2)" may be plotted only for the time phase immediately before the "during oxygen inhalation (O2)" period so that at least the temporal change in the signal values at the "during oxygen inhalation (O2)" period can be recognized.

Figure 8:
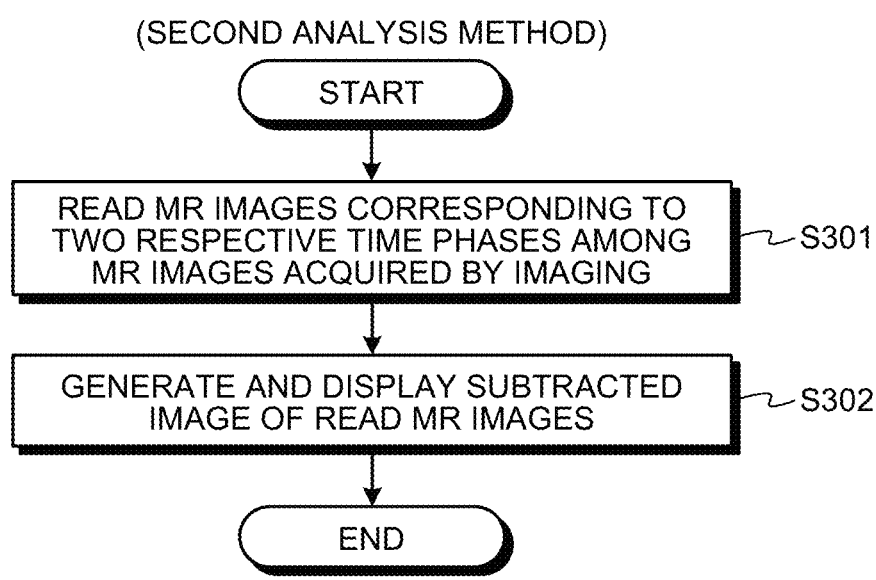
FIG. 8 is a flow chart illustrating a processing procedure of analysis in the first embodiment.

Next, FIG. 8 is a flowchart illustrating a processing procedure of analysis in the first embodiment. As described above, two analysis methods are primarily assumed in the first embodiment, and FIG. 8 illustrates the processing procedure by the second analysis method.

The analyzing unit 133b reads MR images corresponding to at least two respective time phases from the MR images corresponding to the respective time phases that are acquired in the processing procedure of imaging illustrated in FIG. 4 (Step S301). For example, in the first embodiment, the analyzing unit 133b reads from the storage unit 132 an MR image (Pre-O2) corresponding to the time phase immediately before oxygen inhalation starts, an MR image (O2) corresponding to the time phase immediately before oxygen inhalation stops, and an MR image (Post-O2) corresponding to a time phase (a desired time phase) after oxygen inhalation stops.

Subsequently, the analyzing unit 133b generates a subtracted image of the read MR images and displays the subtracted image on the display unit 135 (Step S302). For example, the analyzing unit 133b performs subtraction processing that subtracts the MR image (Pre-O2) corresponding to the time phase before oxygen inhalation from the MR image (O2) corresponding to the time phase during oxygen inhalation. In another example, the analyzing unit 133b performs averaging processing on the MR images corresponding to the respective time phases in one of the periods before, during, and after oxygen inhalation, for example, the MR images (Pre-O2) corresponding to the time phases before oxygen inhalation. Alternatively, the analyzing unit 133b performs subtraction processing that performs subtraction between averaged MR images of at least two respective periods among the periods before, during, and after oxygen inhalation.

Figure 9A:
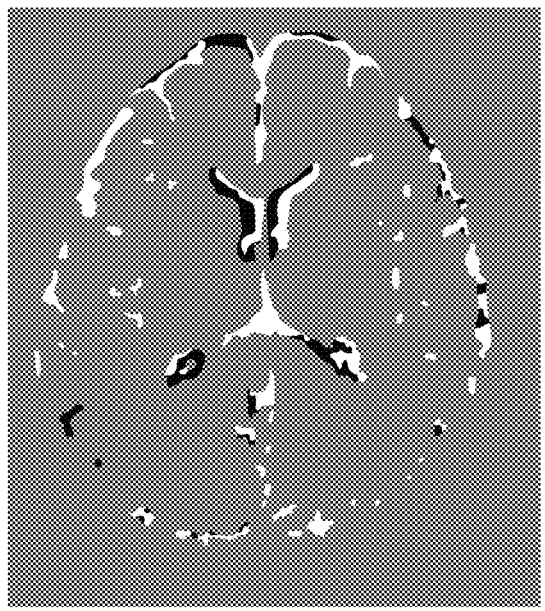
FIGS. 9A and 9B are diagrams for explaining subtracted images in the first embodiment.

FIGS. 9A, 9B, 10A, 10B, and 10C are diagrams for explaining subtracted images in the first embodiment. FIG. 9A is a subtracted image obtained by subtracting an MR image (Pre-O2) corresponding to the time phase immediately before oxygen inhalation starts from an MR image (O2) corresponding to the time phase immediately before oxygen inhalation stops. The contrast enhancement by oxygen provided with oxygen inhalation increases the pixel values of the CSF. Thus, this subtracted image visualizes the CSF in which a change occurs by the contrast enhancement by oxygen in white.

Figure 9B:
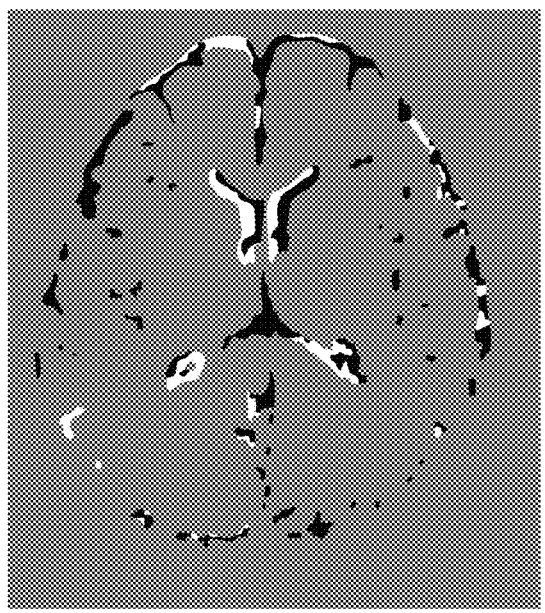

FIG. 9B is a subtracted image obtained by subtracting an MR image (O2) corresponding to the time phase immediately before oxygen inhalation stops from an MR image (Post-O2) corresponding to a time phase after oxygen inhalation stops. The contrast enhancement by oxygen provided with oxygen inhalation is canceled and the pixel values of the CSF decrease. Thus, this subtracted image visualizes the CSF in which a change occurs in black.

The analyzing unit 133b may generate a color mapping image in which colors are assigned depending on the degree of change in pixel values of the CSF, as illustrated in FIGS. 10A, 10B, and 10C. FIG. 10A is an average image of the MR images corresponding to the respective time phases. FIG. 10B is a subtracted image obtained by subtracting an MR image (Pre-O2) corresponding to the time phase immediately before oxygen inhalation starts from an MR image (O2) corresponding to the time phase immediately before oxygen inhalation stops, and also is a color mapping image in which colors are assigned according to the pixel values calculated by the subtraction. FIG. 9C is a subtracted image obtained by subtracting an MR image (O2) corresponding to the time phase immediately before oxygen inhalation stops from an MR image (Post-O2) corresponding to a time phase after oxygen inhalation stops, and also is a color mapping image in which colors are assigned according to the pixel values calculated by the subtraction. A color bar is displayed on the right side of each of the color mapping images in FIGS. 10B and 10C.

In FIGS. 10A, 10B, and 10C, colors are represented by the difference in tone for convenience of explanation. However, the analyzing unit 133b generates a color mapping image according to a color assignment that, for example, assigns colors such as yellow, red, black, blue, and bright blue to the pixels in descending order of the pixel values.

As described above, according to the first embodiment, slice images of the brain are repeatedly acquired at a high time resolution while the subject P is inhaling oxygen, and dynamics of CSF is analyzed from the acquired slice images corresponding to the respective time phases. This enables analysis of a temporal change in the contrast enhancement by oxygen. Furthermore, according to the first embodiment, for example, the CSF region is segmented into the region of a cerebral sulcus portion and the region of a cerebral ventricle portion to be analyzed. This enables analysis of a spatial difference of the contrast enhancement by oxygen. Consequently, according to the first embodiment, the contrast enhancement by oxygen on the CSF can be evaluated in terms of time and/or space, which can bring new clinical findings in diagnosing a cerebrovascular failure and a CSF abnormality, for example.

Second Embodiment

Next, a second embodiment will be explained. The first embodiment exemplifies the use of a pulse sequence based on the fast asymmetric spin echo (FASE) method with an inversion recovery (IR) pulse; however, possible pulse sequences are not limited to this example. The second embodiment exemplifies the use of a pulse sequence by the sequence controller 120 based on the FASE method without an IR pulse. An MRI apparatus 100 according to the second embodiment has the same configuration as that of the MRI apparatus 100 according to the first embodiment.

Figure 11:
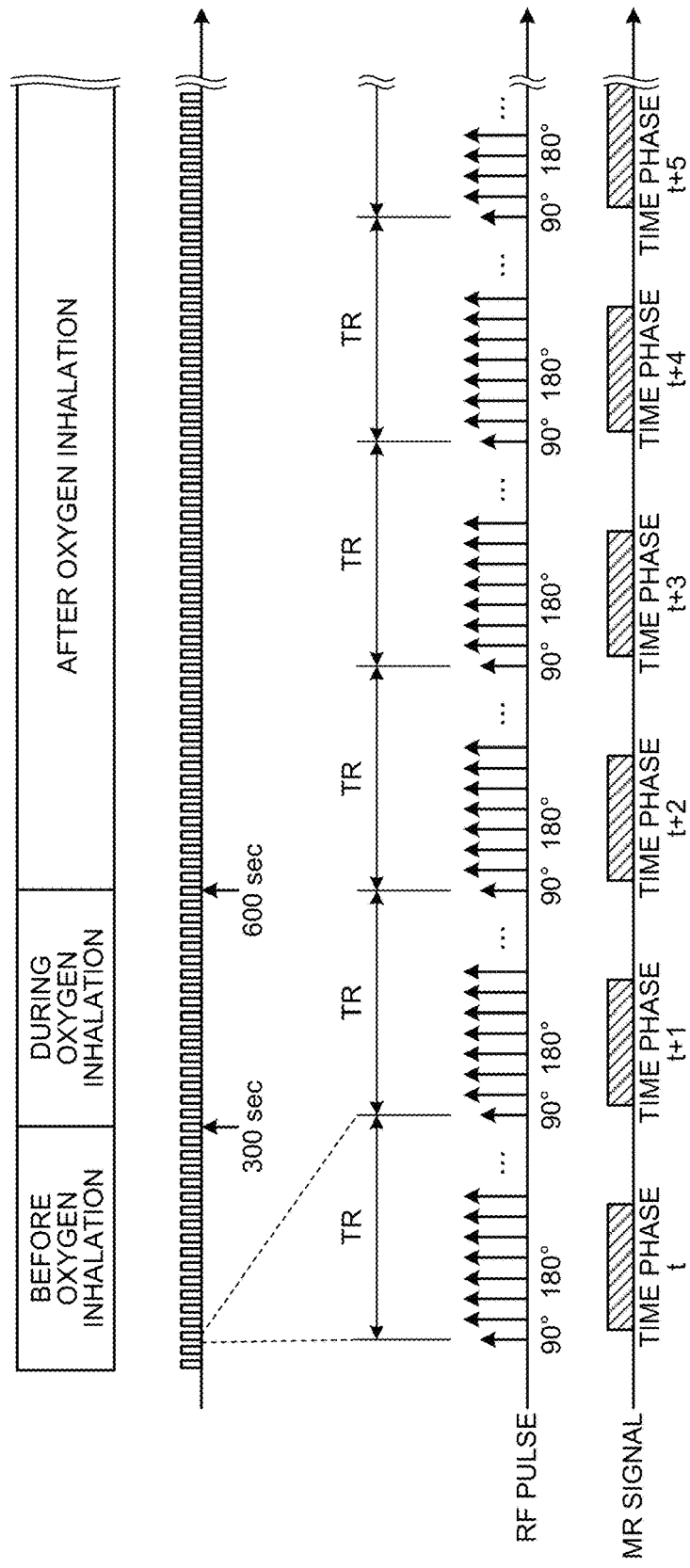
FIG. 11 is a diagram for explaining a pulse sequence in a second embodiment.

FIG. 11 is a diagram for explaining a pulse sequence in the second embodiment. In the second embodiment, an IR pulse is not applied, and thus the recovery of the longitudinal magnetization of the CSF does not need to be considered. The TR can therefore be set shorter than that in the first embodiment, as can be seen by the comparison of FIG. 2 and FIG. 11. As a result, in the second embodiment, a higher time resolution can be set. In the second embodiment, however, due to the absence of inversion of the longitudinal magnetization with an application of an IR pulse, the contrast enhancement by oxygen as a change in the signal values of the CSF is likely to be less than that as a difference to a null point as described in the first embodiment.

Figure 12A:
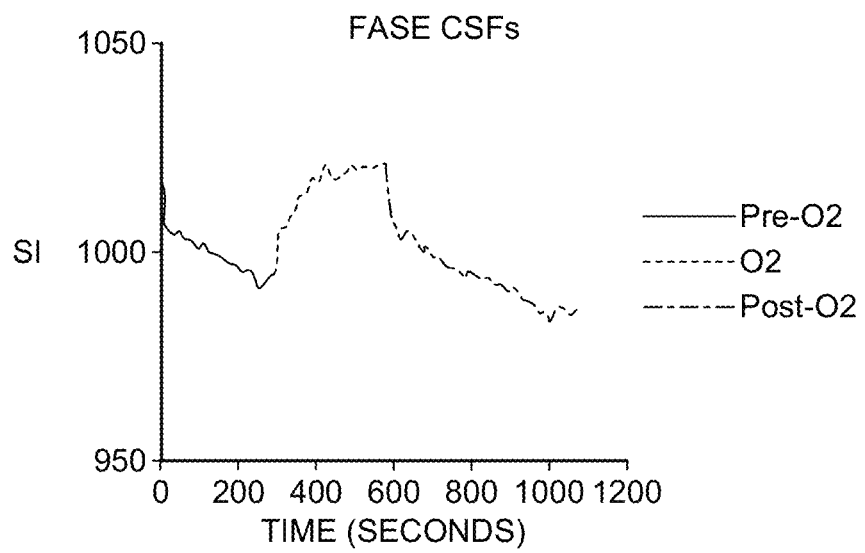
FIGS. 12A and 12B are diagrams for explaining dynamic curves in the second embodiment.
Figure 12B:
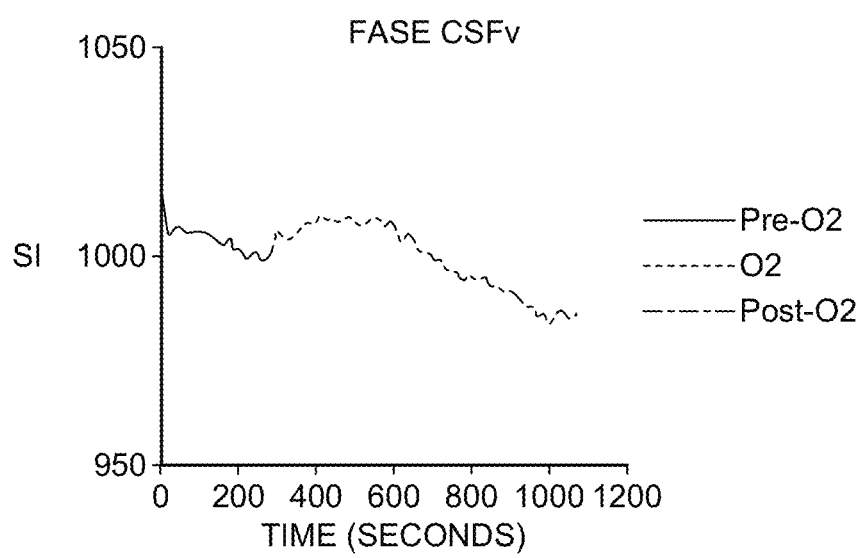

Processing procedures of imaging and analysis in the second embodiment can be implemented in the same manner as those explained in the first embodiment. FIGS. 12A and 12B are diagrams for explaining dynamic curves in the second embodiment, and FIGS. 13A, 13B, and 13C are diagrams for explaining subtracted images in the second embodiment.

In the same manner as in the first embodiment, as illustrated in FIGS. 12A and 12B, the analyzing unit 133b generates a graph for each region of the cerebral sulcus portion and the cerebral ventricle portion, taking the signal intensity as the vertical axis and the elapsed time (seconds) as the horizontal axis, plots the average value of the pixels corresponding to each of the time phases, and connects the plot points with a line to display a dynamic curve. FIG. 12A illustrates a dynamic curve of the region (CSFs) of the cerebral sulcus portion, and FIG. 12B illustrates a dynamic curve of the region (CSFv) of the cerebral ventricle portion.

The dynamic curves illustrated in FIGS. 7A and 7B are different from those in FIGS. 12A and 12B in the scale of the vertical axis. Specifically, it can be recognized that the change in the pixel values in the second embodiment is extremely smaller than that in the first embodiment. It can also be recognized that, by comparing the dynamic curves illustrated in FIGS. 7A and 7B and those in FIGS. 12A and 12B, the dynamic curves in the second embodiment have a higher time resolution.

Figure 13A:
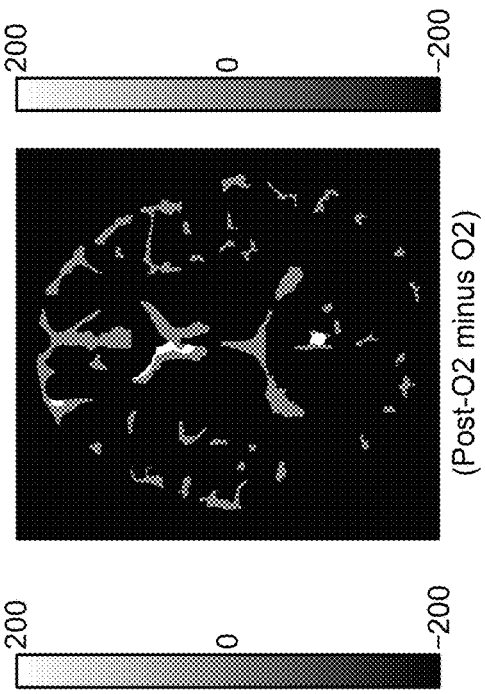
FIGS. 13A, 13B, and 13C are diagrams for explaining subtracted images in the second embodiment.
Figure 13B:
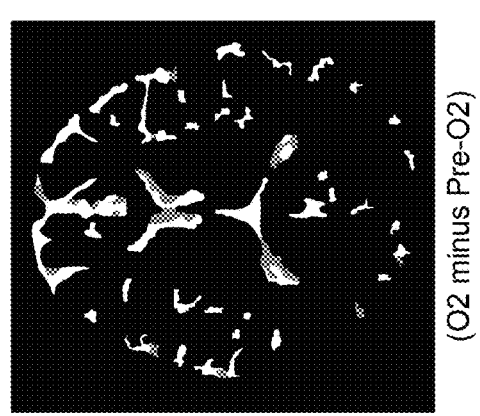
Figure 13C:
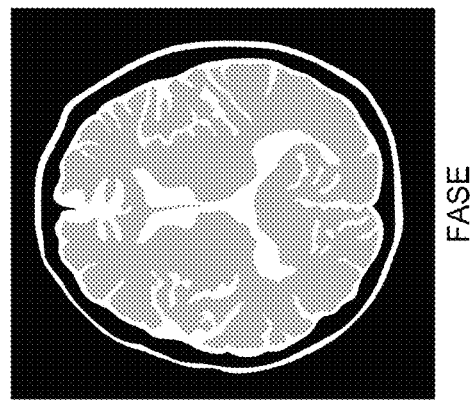

In the same manner as in the first embodiment, the analyzing unit 133b may generate a color mapping image in which colors are assigned depending on the degree of change in pixel values of the CSF, as illustrated in FIGS. 13A, 13B, and 13C. FIG. 13A is an average image of the MR images corresponding to the respective time phases. FIG. 13B is a subtracted image obtained by subtracting an MR image (Pre-O2) corresponding to the time phase immediately before oxygen inhalation starts from an MR image (O2) corresponding to the time phase immediately before oxygen inhalation stops, and also is a color mapping image in which colors are assigned according to the pixel values calculated by the subtraction. FIG. 13C is a subtracted image obtained by subtracting an MR image (O2) corresponding to the time phase immediately before oxygen inhalation stops from an MR image (Post-O2) corresponding to a time phase after oxygen inhalation stops, and also is a color mapping image in which colors are assigned according to the pixel values calculated by the subtraction. The analyzing unit 133b may generate and display subtracted images equivalent to those in FIGS. 9A and 9B, which are not color mapping images, in the same manner as in the first embodiment.

Other Embodiments

Possible embodiments are not limited to those described above.

Acquisition of Three-Dimensional Data

In the embodiments described above, a method is described in which the sequence controller 120 acquires slice images (two-dimensional cross-sectional images) of the brain of a subject in a condition where a supply of oxygen is receivable, at a plurality of time phases in order to understand the dynamics of CSF in the oxygen inhalation process. Possible methods, however, are not limited to that described in the embodiments. Three-dimensional data of the entire brain may be acquired. For example, the second embodiment exemplifies the use of a pulse sequence based on the FASE method without an IR pulse. In this case, the recovery of the longitudinal magnetization of the CSF does not need to be considered, and thus the TR can be set relatively shorter. For example, the sequence controller 120 may acquire three-dimensional data with this pulse sequence. In the description above, the method described in the second embodiment is explained as an example; however, possible method for acquiring the three-dimensional data is not limited to that described in the second embodiment.

In another example, the sequence controller 120 may acquire three-dimensional data using a lower time resolution. In yet another example, the sequence controller 120 may acquire three-dimensional data using a fast imaging method such as the parallel imaging (PI) method.

Segmentation

The embodiments described above exemplify, as an example of segmentation, the case where the CSF region is segmented into the region of a cerebral sulcus portion and the region of a cerebral ventricle portion; however, possible segmentation is not limited to this example. Any segmentation may be applied according to an object of analysis. For example, the CSF region may be segmented into the right brain portion and the left brain portion, or segmented by pixel or by a group of pixels.

Setting of TI with Preparation Scan

The embodiments described above exemplify the case where the TI is set to an appropriate value by referencing the T1 value of the CSF. However, an appropriate TI may be determined with a preparation scan. For example, the sequence controller 120 may perform a preparation scan with changing the TI with reference to the T1 value of the CSF, and then analyzes resultant MR images or MR signals automatically or manually by an operator to obtain an appropriate TI. For example, the sequence controller 120 performs the preparation scan at a stage prior to Step S104 illustrated in FIG. 4. For example, the sequence controller 120 acquires one slice image for each TR by changing the TI for each TR. Thereafter, for example, the sequence controller 120 analyzes the acquired slice images to identify the slice image that reflects (infers) the contrast enhancement by oxygen most significantly, and sets the TI corresponding to the identified slice image as the TI of an imaging scan. Alternatively, for example, the sequence controller 120 may display the acquired slice images on the display unit 135 and receives a specification of a slice image from an operator to identify the slice image that reflects (implies) the contrast enhancement by oxygen most significantly.

Possible methods of such a preparation scan are not limited to those described above. For example, the sequence controller 120 may repeatedly acquire MR signals (e.g., for one segment) with different TIs in one TR. In this case, the sequence controller 120 may, for example, analyze the MR signals for one segment to obtain an appropriate TI, or display the result of the analysis on the display unit 135 to receive a specification from an operator. When the MR signals for one slice image are acquired over a plurality of TRs, the sequence controller 120 may generate a slice image for each TI in the same manner as in the method described above, and, for example, analyze the slice images or display them on the display unit 135 to identify a desired slice image.

Pulse Sequence

The embodiments described above exemplify the pulse sequence by which the contrast enhancement by oxygen is easily observed, such as a pulse sequence based on the FASE method with an IR pulse and a pulse sequence based on the FASE method without an IR pulse. However, possible pulse sequences are not limited to these examples. Any type of pulse sequence may be used as long as it enables observation of the contrast enhancement by oxygen, that is, capable of visualizing a difference in longitudinal magnetization. Any other type of pulse sequence such as that based on the fast spin echo (FSE) method and the balanced steady-state free precession (SSFP) method is similarly applicable.

The embodiments described above exemplify the case where an RF pulse with a flip angle of 90° is applied as an excitation pulse, and then an RF pulse with a flop angle of 180° is applied as a refocus pulse; however, possible pulses are not limited to this example. For example, when MR signals are acquired by the FASE method, either the constant flip (flop) angle (CFA) method or the variable flip (flop) angle (VFA) method may be applied. In case of the CFA method, RF pulses with any desired constant flip (flop) angle are applied, such as an excitation pulse having a flip angle of 90° and a refocus pulse having a flip (flop) angle of 120°. In the case of VFA, RF pulses are applied by changing the flip (flop) angle of refocus pulses. In another example, when MR signals are acquired by the balanced SSFP method, RF pulses with such desired flip angles that establish a steady state are applied, the flip angles being $\alpha°/2, \alpha°, \alpha°, \ldots, \alpha°$, for example.

A Plurality of Oxygen Inhalation

The embodiments described above exemplify the case where the subject P is supplied with oxygen one time and slice images of the brain are repeatedly acquired for the entire of the one oxygen inhalation process. However, possible oxygen inhalation is not limited to this example. The subject P may be repeatedly supplied with oxygen a plurality of times, and slice images of the brain may be repeatedly acquired for the entire of the oxygen inhalation processes. In this case, the analyzing unit 133*b* may generate and display a dynamic curve for the entire oxygen inhalation processes, for example. In another example, the analyzing unit 133*b* may generate and display a subtracted image of MR images corresponding to the same time phase (e.g., MR images (O2) corresponding to the time phase immediately before oxygen inhalation stops) in different oxygen inhalation processes. In another example, the analyzing unit 133*b* may add MR images to each other corresponding to the same time phase in different oxygen inhalation processes and generate a subtracted image of the added images in the same manner as described in the embodiments described above. As described above, the analyzing unit 133*b* can perform analyses different from the embodiments described above, and display the results of the analyses.

Target Imaging Part

Figure 14:
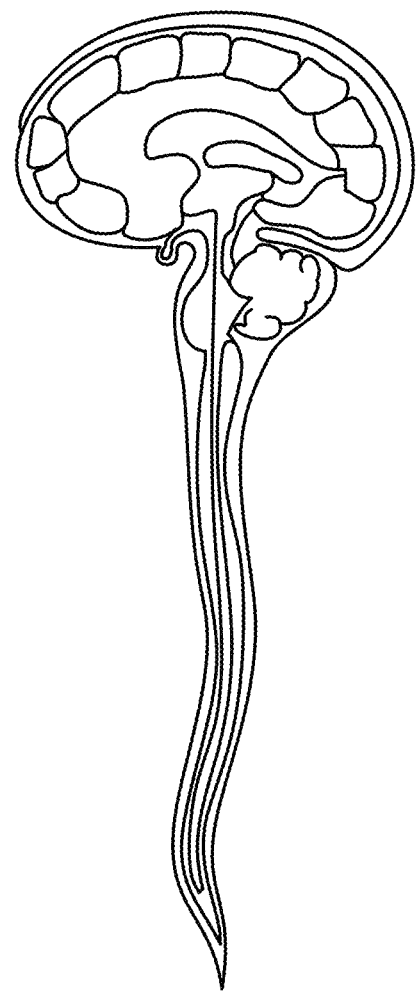
FIG. 14 is a diagram for explaining the flow of CSF.

The embodiments described above exemplify the imaging of dynamics of CSF by taking the "brain" as a target imaging part; however, possible target imaging parts are not limited to that described in the embodiments. FIG. 14 is a diagram for explaining the flow of CSF. As illustrated in FIG. 14, CSF is present in the cerebral ventricles and the subarachnoid space in the brain, and in the spinal subarachnoid space in the spinal canal, and the CSF circulates through those regions. The embodiments described above are thus similarly applicable to a case in which the "spinal cord" is set as the target imaging part.

Analysis of a Plurality of Subjects

The embodiments described above exemplify the case where MR images acquired from one subject are analyzed and the results of the analysis on the one subject are displayed; however, a possible number of subjects is not limited to that described in the embodiments. For example, the analyzing unit 133b may analyze MR images acquired from a plurality of subjects in terms of statistical values such as an average value, the maximum value, and the minimum value, and display the results of the analyses on the subjects. For example, generating analysis results acquired from a plurality of healthy subjects enables a comparison of the analysis results with an analysis result of MR images acquired from one subject, determining whether the one subject is healthy.

Subtraction of Images

The embodiments described above exemplify the case where the analyzing unit 133b calculates a subtracted image between an MR image corresponding to the time phase immediately before oxygen inhalation stops and an MR image corresponding to the time phase immediately before oxygen inhalation starts, or between an MR image corresponding to a time phase after oxygen inhalation stops and an MR image corresponding to the time phase immediately before oxygen inhalation stops; however, possible processing apparatuses are not limited to that described in the embodiments. For example, when calculating a subtracted image, the analyzing unit 133b may use an MR image of any time phase in the period during oxygen inhalation instead of the MR image corresponding to the time phase immediately before oxygen inhalation stops, an MR image of any time phase in the period before oxygen inhalation instead of the MR image corresponding to the time phase immediately before oxygen inhalation starts, and an MR image of any time phase in the period after oxygen inhalation as the MR image corresponding to the time phase after oxygen inhalation stops.

Image Processing Apparatus

The embodiments described above exemplify the case where the MRI apparatus 100 performs various types of processing; however, possible processing apparatuses are not limited to that described in the embodiments. For example, an image processing apparatus or an image processing system including an MRI apparatus 100 and an image processing apparatus may perform the various types of processing described above, in place of the MRI apparatus 100. Examples of the image processing apparatus include work stations, image storing apparatuses (image servers) and viewing tools in picture archiving and communication systems (PACSs), and various types of apparatuses in electronic medical record systems. In this case, for example, the image processing apparatus receives k-space data acquired by the MRI apparatus 100 or MR images reconstructed from the k-space data from the MRI apparatus 100, from an image server via a network or through an input from an operator via a recording medium, and stores them in a storage unit. After that, the image processing apparatus may perform the various types of processing (e.g., the processing performed by the analyzing unit 133b and the processing procedures illustrated in FIG. 5 and FIG. 8) described above on the k-space data or the MR images stored in the storage unit, as processing targets.

Specific Numerical Values and Specific Order of Processing

The specific numerical values (e.g., 300 seconds and 600 seconds) and the specific order of processing (e.g., the processing procedures illustrated in FIGS. 4, 5, and 8) exemplified in the embodiments described above are merely examples in principle.

Computer Program

The instructions indicated in the processing procedures in the embodiments described above may be executed on the basis of a computer program in the form of software. The instructions described in the embodiments above are recorded as a computer-executable program, onto a magnetic disk, an optical disc, a semiconductor memory, or any other similar recording medium. When the computer reads the computer program from the recording medium and causes a CPU to execute the instructions written in the computer program according to the computer program, the computer can implement the same operations as those of the MRI apparatus 100 and the image processing apparatus according to the embodiments described above. Furthermore, the computer may obtain or read the computer program via a network.

According to at least one aspect of the magnetic resonance imaging apparatus and the image processing apparatus, a contrast enhancement by oxygen on cerebrospinal fluid (CSF) can be analyzed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
a sequence controller that, by magnetic resonance imaging using a pulse sequence set according to T1 of cerebrospinal fluid not during an oxygen inhalation time phase, acquires magnetic resonance signals of a target imaging part including cerebrospinal fluid flowing therein of a subject in a condition where a supply of oxygen is receivable, at a plurality of time phases in an oxygen inhalation process of the subject;
a storage unit that stores therein the magnetic resonance signals acquired at the time phases; and
an analyzing unit that analyzes the magnetic resonance signals acquired at the time phases,
wherein the analyzing unit extracts, from magnetic resonance images reconstructed with the respective magnetic resonance signals acquired at the time phases, a region of a cerebral sulcus portion and a region of a cerebral ventricle portion by further segmenting a cerebrospinal fluid region where the cerebrospinal fluid is present, and analyzes each of the extracted regions.

2. The magnetic resonance imaging apparatus according to claim 1, wherein the oxygen inhalation process includes at least one period of periods before, during, and after oxygen inhalation.

3. The magnetic resonance imaging apparatus according to claim 1, wherein the sequence controller acquires the magnetic resonance signals at the time phases at a time resolution at which a temporal change in signal values of the cerebrospinal fluid during oxygen inhalation is analyzable.

4. The magnetic resonance imaging apparatus according to claim 1, wherein the analyzing unit calculates statistical values of signal values of the cerebrospinal fluid in each of the region of a cerebral sulcus portion and the region of a cerebral ventricle portion generates a graph with the calculated statistical values plotted in time series, and displays the generated graph on a display unit.

5. A magnetic resonance imaging apparatus comprising:
a sequence controller that acquires magnetic resonance signals of a target imaging part including cerebrospinal fluid flowing therein of a subject in a condition where a supply of oxygen is receivable, at a plurality of time phases in an oxygen inhalation process of the subject;
a storage unit that stores therein the magnetic resonance signals acquired at the time phases; and
an analyzing unit that analyzes the magnetic resonance signals acquired at the time phases,
wherein the analyzing unit calculates a subtracted image of magnetic resonance images reconstructed with the magnetic resonance signals corresponding to at least two respective time phases of the magnetic resonance signals acquired at the respective time phases, and displays the calculated subtracted image on a display unit.

6. The magnetic resonance imaging apparatus according to claim 5, wherein the analyzing unit calculates a subtracted image between a magnetic resonance image of a period during oxygen inhalation and a magnetic resonance image of a period before oxygen inhalation, and displays the calculated subtracted image on the display unit.

7. The magnetic resonance imaging apparatus according to claim 5, wherein the analyzing unit calculates a subtracted image between a magnetic resonance image of a period after oxygen inhalation and a magnetic resonance image of a period during oxygen inhalation, and displays the calculated subtracted image on the display unit.

8. An image processing apparatus comprising:
a storage unit that stores therein magnetic resonance signals of a target imaging part including cerebrospinal fluid flowing therein, the signals being acquired by a magnetic resonance imaging apparatus, by magnetic resonance imaging using a pulse sequence set according to T1 of cerebrospinal fluid not during an oxygen inhalation time phase, at a plurality of time phases in an oxygen inhalation process of a subject in a condition where a supply of oxygen is receivable, or stores therein magnetic resonance images reconstructed from the magnetic resonance signals; and
an analyzing unit that analyzes a temporal change in signal values of the cerebrospinal fluid during oxygen inhalation based on the magnetic resonance signals or the magnetic resonance images,
wherein the analyzing unit extracts, from magnetic resonance images reconstructed with the stored respective magnetic resonance signals acquired at the time phases or the stored magnetic resonance images, a region of a cerebral sulcus portion and a region of a cerebral ventricle portion by further segmenting a cerebrospinal fluid region where the cerebrospinal fluid is present, and analyzes each of the extracted regions.

9. An image processing apparatus comprising:
a storage unit that stores therein magnetic resonance signals of a target imaging part including cerebrospinal fluid flowing therein, the signals being acquired by a magnetic resonance imaging apparatus at a plurality of time phases in an oxygen inhalation process of a subject in a condition where a supply of oxygen is receivable, or magnetic resonance images reconstructed from the magnetic resonance signals; and
an analyzing unit that analyzes a temporal change in signal values of the cerebrospinal fluid during oxygen inhalation based on the magnetic resonance signals or the magnetic resonance images,
wherein the analyzing unit calculates a subtracted image of magnetic resonance images reconstructed with the stored magnetic resonance signals corresponding to at least two respective time phases or a subtracted image of the stored magnetic resonance images corresponding to at least two respective time phases, and displays the calculated subtracted image on a display unit.

10. A magnetic resonance imaging method comprising:
acquiring, based upon magnetic resonance imaging using a pulse sequence set according to T1 of cerebrospinal fluid not during an oxygen inhalation time phase, magnetic resonance signals of a target imaging part including cerebrospinal fluid flowing therein of a subject in a condition where a supply of oxygen is receivable, at a plurality of time phases in an oxygen inhalation process of the subject; and
analyzing the magnetic resonance signals acquired at the time phases,
wherein the analyzing of the magnetic resonance signals includes extracting, from magnetic resonance images reconstructed with the respective magnetic resonance signals acquired at the time phases, a region of a cerebral sulcus portion and a region of a cerebral ventricle portion by further segmenting a cerebrospinal fluid region where the cerebrospinal fluid is present, and analyzing each of the extracted regions.

11. A magnetic resonance imaging method comprising:
acquiring magnetic resonance signals of a target imaging part including cerebrospinal fluid flowing therein of a subject in a condition where a supply of oxygen is receivable, at a plurality of time phases in an oxygen inhalation process of the subject; and
analyzing the magnetic resonance signals acquired at the time phases,
wherein the analyzing of the magnetic resonance signals includes calculating a subtracted image of magnetic resonance images reconstructed with the magnetic resonance signals corresponding to at least two respective time phases of the magnetic resonance signals acquired at the respective time phases, and displaying the calculated subtracted image on a display unit.

12. An image processing method comprising:
obtaining magnetic resonance signals of a target imaging part including cerebrospinal fluid flowing therein, the signals being acquired by a magnetic resonance imaging apparatus, based upon magnetic resonance imaging with an imaging condition set based on T1 of cerebrospinal fluid not during an oxygen inhalation time phase, at a plurality of time phases in an oxygen inhalation process of a subject in a condition where a supply of oxygen is receivable, or obtaining magnetic resonance images reconstructed from the magnetic resonance signals; and
analyzing a temporal change in signal values of the cerebrospinal fluid during oxygen inhalation based on the magnetic resonance signals or the magnetic resonance images,
wherein the analyzing of the temporal change in the signal values of the cerebrospinal fluid includes extracting, from magnetic resonance images reconstructed with the obtained respective magnetic resonance signals acquired at the time phases or the obtained magnetic resonance images, a region of a cerebral sulcus portion and a region of a cerebral ventricle portion by further segmenting a cerebrospinal fluid region where the cerebrospinal fluid is present, and analyzing each of the extracted regions.

13. An image processing method comprising:
obtaining magnetic resonance signals of a target imaging part including cerebrospinal fluid flowing therein, the signals being acquired by a magnetic resonance imaging apparatus at a plurality of time phases in an oxygen inhalation process of a subject in a condition where a supply of oxygen is receivable, or magnetic resonance images reconstructed from the magnetic resonance signals; and
analyzing a temporal change in signal values of the cerebrospinal fluid during oxygen inhalation based on the magnetic resonance signals or the magnetic resonance images,
wherein the analyzing of the temporal change in the signal values of the cerebrospinal fluid includes calculating a subtracted image of magnetic resonance images reconstructed with the obtained magnetic resonance signals corresponding to at least two respective time phases or a subtracted image of the obtained magnetic resonance images corresponding to at least two respective time phases, and displaying the calculated subtracted image on a display unit.

* * * * *

UNITED STATES PATENT AND TRADEMARK OFFICE
CERTIFICATE OF CORRECTION

PATENT NO. : 10,180,480 B2
APPLICATION NO. : 14/463023
DATED : January 15, 2019
INVENTOR(S) : Fushimi et al.

Page 1 of 1

It is certified that error appears in the above-identified patent and that said Letters Patent is hereby corrected as shown below:

On the Title Page

(73) Assignee should read: TOSHIBA MEDICAL SYSTEMS CORPORATION,
Otawara-shi, Tochigi (JP)
KYOTO UNIVERSITY, Kyoto-shi, Kyoto (JP)

Signed and Sealed this
Seventh Day of May, 2019

Andrei Iancu
*Director of the United States Patent and Trademark Office*